(12) United States Patent
Penner et al.

(10) Patent No.: US 7,960,129 B2
(45) Date of Patent: Jun. 14, 2011

(54) ASSAYS AND METHODS FOR DETERMINING STIM2 ACTIVITY

(75) Inventors: Reinhold Penner, Honolulu, HI (US); Andrea Fleig, Honolulu, HI (US)

(73) Assignee: The Queen's Medical Center, Honolulu, HI (US)

( * ) Notice: Subject to any disclaimer, the term of this patent is extended or adjusted under 35 U.S.C. 154(b) by 110 days.

(21) Appl. No.: 12/053,329

(22) Filed: Mar. 21, 2008

(65) Prior Publication Data

US 2009/0023177 A1 Jan. 22, 2009

Related U.S. Application Data

(60) Provisional application No. 60/896,581, filed on Mar. 23, 2007.

(51) Int. Cl.
*G01N 33/53* (2006.01)
*C12Q 1/02* (2006.01)

(52) U.S. Cl. .......................... 435/7.2; 435/29
(58) Field of Classification Search .................. None
See application file for complete search history.

(56) References Cited

FOREIGN PATENT DOCUMENTS
WO WO 2004/078995 9/2004

OTHER PUBLICATIONS

Soboloff et al. ORAI1 and STIM2 Reconstitute Store-Operated Calcium Channel Function; The Journal of Biological Chemistry, vol. 281, No. 30 (2006) pp. 20661-20665.*

Soboloff et al. STIM2 Is an Inhibitor of STIM1-Mediated Store-Operated Calcium Entry; Current Biology, vol. 16 (2006) pp. 1465-1470.*

Hermosura et al. Dissociation of the Store-Operated Calcium Current ICRAC and the MG-Nucleotide-Regulated Metal Ion Current Magnum; Journal of Physiology, vol. 539.2 (2002) pp. 445-458.*

Mathes et al. Calcium Release-Activated Calcium Current (ICRAC) Is a Direct Target for Sphingosine; The Journal of Biological Chemistry, vol. 273, No. 39 (1998) pp. 25020-25030.*

Parvez et al. STIM2 Protein Mediates Distinct Store-Dependent and Store-Independent Modes of CRAC Channel Activation; The FASEB Journal, vol. 22 (2008) pp. 752-761.*

Prakriya et al. Potentiation and Inhibition of CA2+ Release-Activated CA2+ Channels by 2-Aminoethyldiphenyl Borate (2-APB) Occurs Independently of IP3 Receptors; Journal of Physiology, vol. 536, No. 1 (2001) pp. 3-19.*

Palade, P., "Drug-Induced Calcium Release from Isolated Sarcoplasmic Reticulum III. Block of Calcium-Induced Calcium Release by Organic Plyamines," J. of Biological Chemistry, v. 262, n. 13, p. 6149-6154, (1987).

Ruano, Yolanda et al., Identification of Novel Candidate Target Genes in Amplicons of Glioblastoma Multiforme Tumors Detected by Expression and CGH Microarray Profiling. Molecular Cancer, Biomed Central, v. 5, n. 1, p. 39, Sep. 26, 2006.

Soboloff, Jonathan, et al., "Orai1 and STIM Reconstitute Store-Operated Calcium Channel Function," J. of Biological Chemistry, v. 281, n. 30, p. 20661-20665, Jul. 30, 2006.

Soboloff, Jonathan, et al., "STIM2 is an Inhibitor of STIM1-Mediated Store-Operated Ca<2+> Entry," Current Biology, Current Science, v. 16, n. 14, p. 1465-1470, Jul. 25, 2006.

* cited by examiner

*Primary Examiner* — Rebecca E Prouty
*Assistant Examiner* — Paul C Martin
(74) *Attorney, Agent, or Firm* — Morgan Lewis & Bockius LLP

(57) ABSTRACT

The present invention provides assays and methods for determining levels of STIM2 activity, thus providing tools for the characterization and study of the regulation of intracellular calcium levels.

6 Claims, 4 Drawing Sheets

ASSAYS AND METHODS FOR DETERMINING STIM2 ACTIVITY

CROSS REFERENCE TO RELATED APPLICATIONS

The present application claims the benefit of the filing date of U.S. Provisional Patent Application No. 60/896,581, filed Mar. 23, 2007, which is hereby incorporated by reference in its entirety for all purposes.

STATEMENT REGARDING FEDERALLY SPONSORED RESEARCH OR DEVELOPMENT

This invention was made with government support from NIH grant R01-AI050200. The government has certain rights in the invention.

FIELD OF THE INVENTION

The invention relates generally to CRAC channels and their association with STIM1 and STIM2. In particular, this invention encompasses assays and methods for determining STIM2 activity in a cell.

BACKGROUND OF THE INVENTION

Changes in intracellular free calcium concentration ($[Ca^{2+}]_i$) represent the most wide-spread and important signaling event for regulating a plethora of cellular responses. Many cell types employ store-operated $Ca^{2+}$ entry as their principal pathway for $Ca^{2+}$ influx. This mechanism is engaged following $Ca^{2+}$ release from stores, where the depleted stores lead to activation of Calcium Release-Activated $Ca^{2+}$ (CRAC) channels. Recent work has identified stromal interaction molecule (STIM1) and CRAC Modulator 1 (CRACM1 or Orai1) as essential components for functional store operated $Ca^{2+}$ entry. STIM1 and CRACM1 are sufficient to reconstitute and amplify CRAC currents in heterologous expression systems. In mammals, there exist several homologs of these proteins: STIM1 and STIM2 in the endoplasmic reticulum and CRACM1, CRACM2, and CRACM3 in the plasma membrane. The role of STIM2 in store operated $Ca^{2+}$ entry appears to be complex and remains incompletely understood.

A need exists, therefore, for a method by which the level and role of STIM2 on the activity of CRAC channels can be assessed.

SUMMARY OF THE INVENTION

Accordingly, the present invention provides assays and methods for determining activity of STIM2 in a cell.

In one aspect, the invention provides an assay for STIM2 activity in a cell comprising measuring Icrac activity. In a preferred aspect of this assay, 2-APB is applied to the cell, and an increase in Icrac activity in response to this application of 2-APB indicates a level of STIM2 activity in said cell. In a further aspect, the increase in Icrac activity occurs in the absence of calcium store depletion.

In another aspect, the invention provides an assay for STIM2 activity in a cell comprising measuring Icrac activity after application of an aminoglycoside antibiotic. In one aspect of the assay, suppression of Icrac activity by the antibiotic indicates a level of STIM2 activity in the cell.

In a further aspect, the invention provides an assay for aminoglycoside antibiotics that have immunosuppressive properties.

DETAILED DESCRIPTION OF THE INVENTION

Abbreviations

Figure 1:
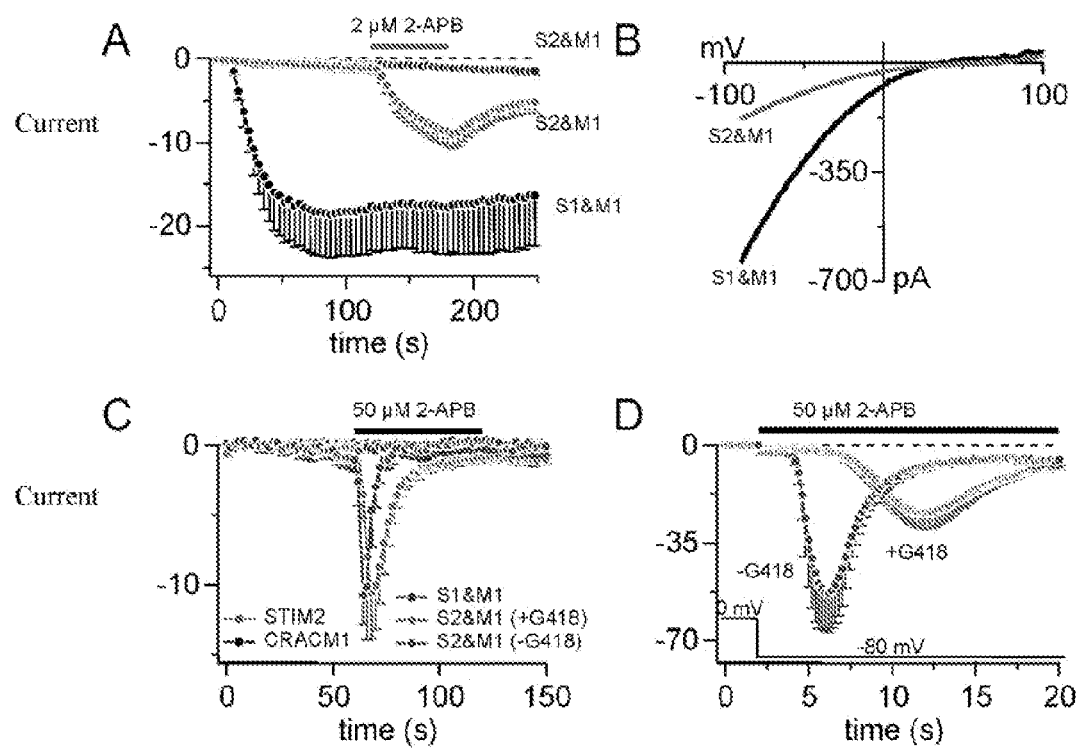
FIG. 1: (A) Average CRAC current densities induced by $IP_3$ (20 µM) in STIM1+CRACM1 cells, STIM2+CRACM1 cells, and STIM2+CRACM1 cells stimulated by 2 µM 2-APB. (B) Representative current-voltage (I/V) relationships of CRAC currents induced by $IP_3$ (20 µM) in STIM1+ CRACM1-expressing cells or 2 µM 2-APB in STIM2+ CRACM1-expressing cells shown in panel A. (C) Average CRAC current densities in HEK293 cells expressing STIM2 alone (n=5), CRACM1 alone (n=3), STIM1+CRACM1 (n=8), and STIM2+CRACM1 grown in the presence (n=9) or absence (n=6) of G418. In all cells, $[Ca^{2+}]_i$ was buffered to 150 nM using 20 mM BAPTA and 8 mM $CaCl_2$. (D) High-resolution average CRAC currents at −80 mV in STIM2+ CRACM1 cells grown in the presence (n=7) or absence (n=5) of G418 induced by 50 µM 2-APB.

"2-APB" refers to 2-aminoethoxydiphenyl borate.
"IP$_3$" refers to inositol 1,4,5-triphosphate.
"STIM1" refers to Stromal Interaction Molecule 1. Similarly, "STIM2" refers to Stromal Interaction Molecule 2.
"CRAC channel" refers to Calcium Release-Activated Ca$^{2+}$ channel.

DEFINITIONS

The singular forms "a," "an," and "the" include plural references, unless the context clearly dictates otherwise. Thus, for example, references to a composition for delivering "a drug" include reference to one, two or more drugs.

"STIM2 activity" refers to the effects of STIM2 on CRAC channel function, including but not limited to current amplitude, activation and inactivation kinetics, and pharmacology.

"Icrac activity" refers to activity of calcium release activated calcium channels. Such activity can be observed and quantified by methods known in the art, including fluorescence imaging of calcium levels and electrophysiological measurements of ionic current, including calcium current.

CRACM1, CRACM2 and CRACM3 are CRAC channel homologs.

Introduction

CRAC channels are activated by the release of calcium from intracellular stores, particularly from the endoplasmic reticulum. These channels are key factors in the regulation of a wide range of cellular function, including muscle contraction, protein and fluid secretion and control over cell growth and proliferation.

Studies of heterologously expressed CRAC channel homologs have shown that activation of these channels is modulated by a number of cellular factors, including STIM1 and STIM2. STIM1 acts as a calcium sensor in the endoplasmic reticulum that moves toward the plasma membrane to bind and activate CRACM1 channels following store depletion. The activity of STIM2 has not been as fully characterized as that of STIM1, but early studies suggest that STIM2 has a very different effect on CRAC channel activity than STIM1. The instant invention provides assays and methods which utilize the function properties of CRAC channels associated with STIM2 to determine levels of STIM2 activity in a cell.

Pharmacology 2-aminoethoxydiphenyl borate (2-APB) is a compound that has facilitatory effects on CRAC currents at low doses ($\leq 5$ µM), but inhibits them at high doses ($\geq 10$ µM). When cells are stimulated with a higher concentration, for example, 50 µM 2-APB, CRAC currents activate rapidly and then are immediately curtailed by the inhibitory action of 2-APB, which results in a transient surge of inward current (FIG. 1C). When IP$_3$ is omitted and [Ca$^{2+}$]$_i$ is buffered to avoid store depletion, it is possible to induce current upon application of 2-APB, but this effect is specific to cells overexpressing STIM2 and CRACM1, and is not observed in cells overexpressing either STIM2 or CRACM1 alone or in cells overexpressing a combination of STIM1 and CRACM1 (FIG. 1C). Thus, it is possible to use the differences in pharmacology between STIM1- and STIM2-associated CRAC channels to assay the level of STIM2 activity in a cell. (FIGS. 1C and 1D).

In one aspect, the invention takes advantage of these pharmacological properties to provide an assay for STIM2 activity in a cell. This assay includes measuring Icrac activity in response to 2-APB. An increase in Icrac activity in response to 2-APB indicates a level of STIM2 activity in said cell. In a further aspect, this response to 2-APB occurs in the absence of calcium store depletion.

STIM2 activity may also be modulated by the pharmacological effects of aminoglycoside antibiotics, such as streptomycin, gentamicin, tobramycin, amikacin, ciprofloxacin, aztreonam, ceftazidime, cefotaxime, trimethoprim-sulfamethoxazole, piperacillin-tazobactam, ticarcillin-clavulanate, and G418 (also known as geneticin).

The presence of G418 does not appear to compromise STIM1-dependent activation of CRACM1 currents. STIM1 cells grown in G418 produce CRACM1 currents with similar properties to those produced by cells unexposed to the antibiotic. However, STIM2-mediated signaling is compromised by G418. HEK293 cells grown in the absence of G418 exhibit enhanced responses to 2-APB. Furthermore, STIM2 cells do not respond to IP$_3$-induced store depletion when exposed to the antibiotic, but cells grown in the absence of G418 do show activation of CRACM1 currents upon store depletion. This effect is not seen in cells coexpressing STIM1 and CRACM1.

Thus, in another aspect, the invention provides an assay for STIM2 activity in a cell comprising measuring Icrac activity after application of an aminoglycoside antibiotic. In one embodiment of the assay, suppression of Icrac activity by the antibiotic indicates a level of STIM2 activity in the cell. In a preferred embodiment, suppression of Icrac activity by the antibiotic occurs through inhibition of store depletion-induced activation of Icrac via STIM2. In a preferred embodiment of the invention, the effect of the antibiotic activity is overcome by application of 2-APB; this action by 2-APB serves as a further indication of STIM2 activity in a cell.

Certain aminoglycoside antibiotics, such as doxorubicin, have been shown to have immunosuppressive effects, particularly when used in combination with cytokines such as interleukin-2. (Ewens et al., *Cancer Res.*, (2006), 66(10):5419-26). Thus, the assays of the present invention can be used to screen for aminoglycoside antibiotics with immunosuppressive effects by identifying aminoglycoside antibiotics that suppress Icrac activity.

Overexpression of STIM2 is Associated with Brain Malignancies

Brain malignancies such as glioblastoma multiforme are characterized by complex structural and genetic alterations. Studies of gene copy number changes in glioblastoma multiforme have shown that certain genes, including STIM2, are overexpressed in these malignancies, indicating a potential role for these molecules in the pathogenesis of these tumors. (Ruana et al., *Molecular Cancer*, (2006), 5.39.) Other studies have shown that STIM2 plays a role in the development of cerebellar neurons, particularly in the elaboration of pontine neurites. (Hansen et al., *Brain Res. Mol. Brain. Res.* (2004), 124(2):165-77). Identification of STIM2 activity can thus be used to characterize and diagnose brain malignancies and certain aspects of neural development.

In one embodiment of the invention, the cell used in an assay of STIM2 activity is derived from a mammalian subject. In a preferred embodiment, the cell is derived from the brain of said mammalian subject, and the presence of STIM2 activity indicates a brain malignancy.

STIM2 and the Immune System

CRAC channels are found throughout the cells of the immune system, including T lymphocytes and B cells. As modulators of CRAC channel functions, STIM1 and STIM2 also play an important role in the functional properties of these cells. Thus, the assays of the present invention can be utilized to screen for agents which affect the immune system.

The present invention may be better understood by reference to the following non-limiting Examples, which are provided as exemplary of the invention. The following examples are presented in order to more fully illustrate preferred embodiments of the invention, but should in no way be construed as limiting the broad scope of the invention.

EXAMPLES

Example I

Heterologous Co-Expression of STIM1 or STIM2 with CRACM1

Figure 4:
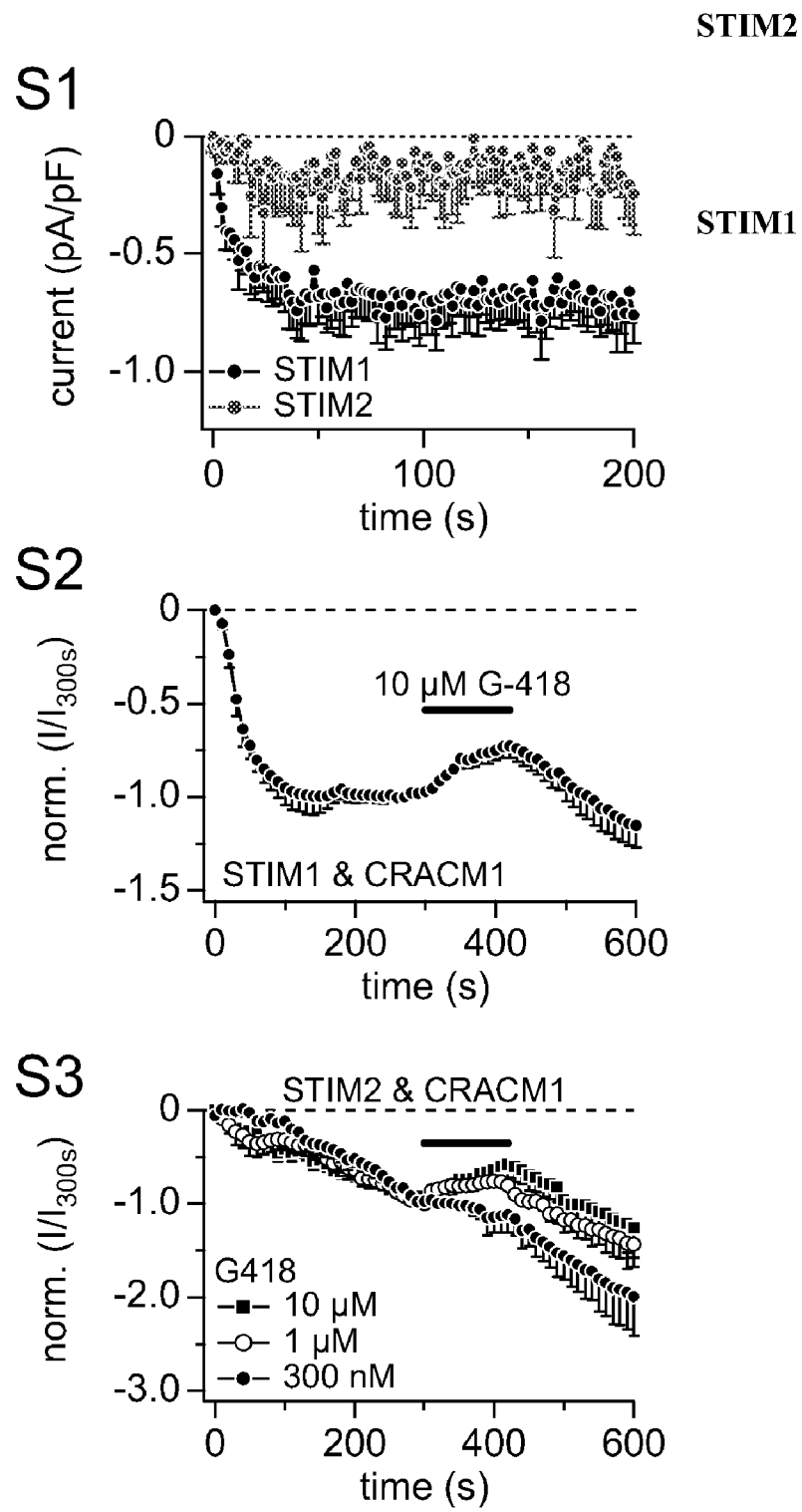
FIG. 4: Average CRAC current densities at −80 mV in cells stably over-expressing STIM1 or STIM2 in response to 20 µM IP$_3$, [Ca$^{2+}$]$_i$ was clamped to near zero with 20 mM BAPTA. Data demonstrate that STIM1 overexpression slightly increases and STIM2 overexpression slightly decreases CRAC currents relative to wt HEK293 cells, which generate current densities of ~0.5 pA/pF. (S2) Average CRAC currents in STIM1+CRACM1 cells (n=7) grown in the presence of G418. Pipette solutions contained IP$_3$ (20 µM) and 10 µM G418, demonstrating that these cells are largely insensitive to intracellular G418. Extracellular application of 10 µM G418 caused a small and reversible reduction in CRAC current. (S3) Average CRAC currents in STIM1+CRACM1 cells (n=7) grown without G418. Pipette solutions contained IP$_3$ (20 µM) to activate biphasic CRAC currents. The bar indicates extracellular application of various concentrations of G418. These caused a small and reversible reduction in CRAC current: 300 nM (filled circles, n=3), 1 µM (open circles, n=4) and 10 µM (filled squares, n=5).

Experiments with HEK293 cells stably overexpressing STIM1 or STIM2 confirmed that both proteins slightly modify endogenous $I_{CRAC}$. In response to $Ca^{2+}$ store depletion by inositol 1,4,5-triphosphate ($IP_3$), STIM2-expressing cells showed reduced $I_{CRAC}$ (~0.2 pA/pF) and STIM1-expressing cells showed slightly increased $I_{CRAC}$ (~0.8 pA/pF) compared to wild-type cells (~0.5 pA/pF) (FIG. 4). STIM1 cells generated large CRAC currents, whereas STIM2 cells did not (FIG. 1A). In contrast to previous reports, under these conditions there was no readily discernable constitutive activity of CRAC channels, although a small basal CRAC current of <1 pA/pF at break-in could have gone unnoticed. However, there was a small CRAC current that developed very slowly, on average amounting to about −1 pA/pF at −80 mV.

Patch-clamp experiments were performed in the tight-seal whole-cell configuration at 21-25° C. High-resolution current recordings were acquired using the EPC-9 (HEKA). Voltage ramps of 50 ms duration spanning a range of −100 to +100 mV were delivered from a holding potential of 0 mV at a rate of 0.5 Hz over a period of 100-700 sec. All voltages were corrected for a liquid junction potential of 10 mV (3 mV with Cl⁻ as main internal anion). Currents were filtered at 2.9 kHz and digitized at 100 μs intervals. Capacitive currents were determined and corrected before each voltage ramp. Extracting the current amplitude at −80 mV from individual ramp current records assessed the low-resolution temporal development of currents. Where applicable, statistical errors of averaged data are given as means±S.E.M. with n determinations. Standard external solutions were as follows (in mM): 120 NaCl, 10 CsCl, 2.8 KCl, 2 MgCl$_2$, 10 CaCl$_2$, 10 TEA-Cl, 10 HEPES, 10 glucose, pH 7.2 with NaOH, 300 mOsm. In some experiments, 2 μM or 50 μM 2-aminoethyldiphenyl borate (2-APB) or 10 μM G418 were added to the standard external solution and applied through wide-tipped puffer pipettes. Standard internal solutions were as follows (in mM): 120 Cs-glutamate, 8 NaCl, 10 Cs-BAPTA, 3 MgCl$_2$, 10 HEPES, 0.02 IP$_3$, pH 7.2 with CsOH, 300 mOsm. As indicated in the figure legends, for some experiments $[Ca^{2+}]_i$ was buffered to 150 nM by 20 mM Cs•BAPTA and 8 mM CaCl$_2$ or 20 mM Cs•EGTA and 8.9 mM CaCl$_2$. For passive-depletion experiments, the internal solution was supplemented with Cs•BAPTA in the absence of IP$_3$ and $Ca^{2+}$. In some experiments, Cs-glutamate and Cs•BAPTA were equimolarly replaced by KCl and K•BAPTA. In others, G418, Na•ATP and Na•GTP or calmodulin were added to intracellular solutions as specified in the figure legends. All chemicals were purchased from Sigma-Aldrich Co.

For fluorescence measurements, cells grown on coverslips were placed in external solution containing (in mM): 107 NaCl, 7.2 KCl, 1 CaCl$_2$, 1.2 MgCl$_2$, 11.5 glucose, 10 HEPES, pH 7.2 with NaOH and loaded with fura-2 acetoxymethylester (2 mM) for 30 min at 20° C. Cells were washed, and dye was allowed to de-esterify for a minimum of 30 min at 20° C. Approximately 95% of the dye was confined to the cytoplasm as determined by the signal remaining after saponin permeabilization. Cells on coverslips were placed in external solution in the absence or presence of 1 mM CaCl$_2$. $Ca^{2+}$ measurements were made using an InCyt dual-wavelength fluorescence imaging system (Intracellular Imaging Inc.). Fluorescence emission at 505 nm was monitored with excitation at 340 and 380 nm; intracellular $Ca^{2+}$ measurements are shown as 340/380 nm ratios obtained from groups (35 to 45) of single cells. The details of these $Ca^{2+}$ measurements were described previously. All measurements shown are representative of a minimum of three independent experiments.

Example II

Pharmacology of CRACM1 Currents in the Presence of STIM1 and STIM2

Despite the lack of IP$_3$-induced CRACM1 currents, large CRACM1 currents with typically inwardly rectifying current-voltage relationships (FIG. 1, A and B) could be induced by external application of 2 mM 2-aminoethoxydiphenyl borate (2-APB, FIG. 1A). 2-APB is a compound that has facilitatory effects on CRAC currents at low doses (≦5 μM), but inhibits them at high doses (≧10 mM). Indeed, when stimulating cells with a higher concentration of 50 mM 2-APB, CRAC currents activated rapidly and were immediately curtailed by the inhibitory action of 2-APB, resulting in a transient surge in inward current (FIG. 1C). IP$_3$ was omitted from the patch pipette and $[Ca^{2+}]_i$ was buffered to 150 nM to avoid any kind of store depletion, so the 2-APB effect observed here did not require store depletion.

To better resolve the kinetics of this response, high-resolution recordings of the 2-APB effect were obtained at a fixed membrane potential of 80 mV. As can be seen in FIG. 1D, the 2-APB-induced current activated within a few seconds and was rapidly blocked, producing a transient current. This 2-APB-induced effect was specific to cells over-expressing STIM2 and CRACM1, and was not observed in HEK293 cells that over-expressed STIM2 or CRACM1 alone or a combination of STIM1 and CRACM1 (FIG. 1C).

The above results suggest that STIM2 cannot activate CRACM1 channels in response to $IP_3$-induced store depletion, whereas 2-APB will cause significant CRACM1 activation and this mechanism requires the presence of STIM2.

Example III

Effect of Aminoglycoside Antibiotic on STIM1 and STIM2 Activity

Figure 2:
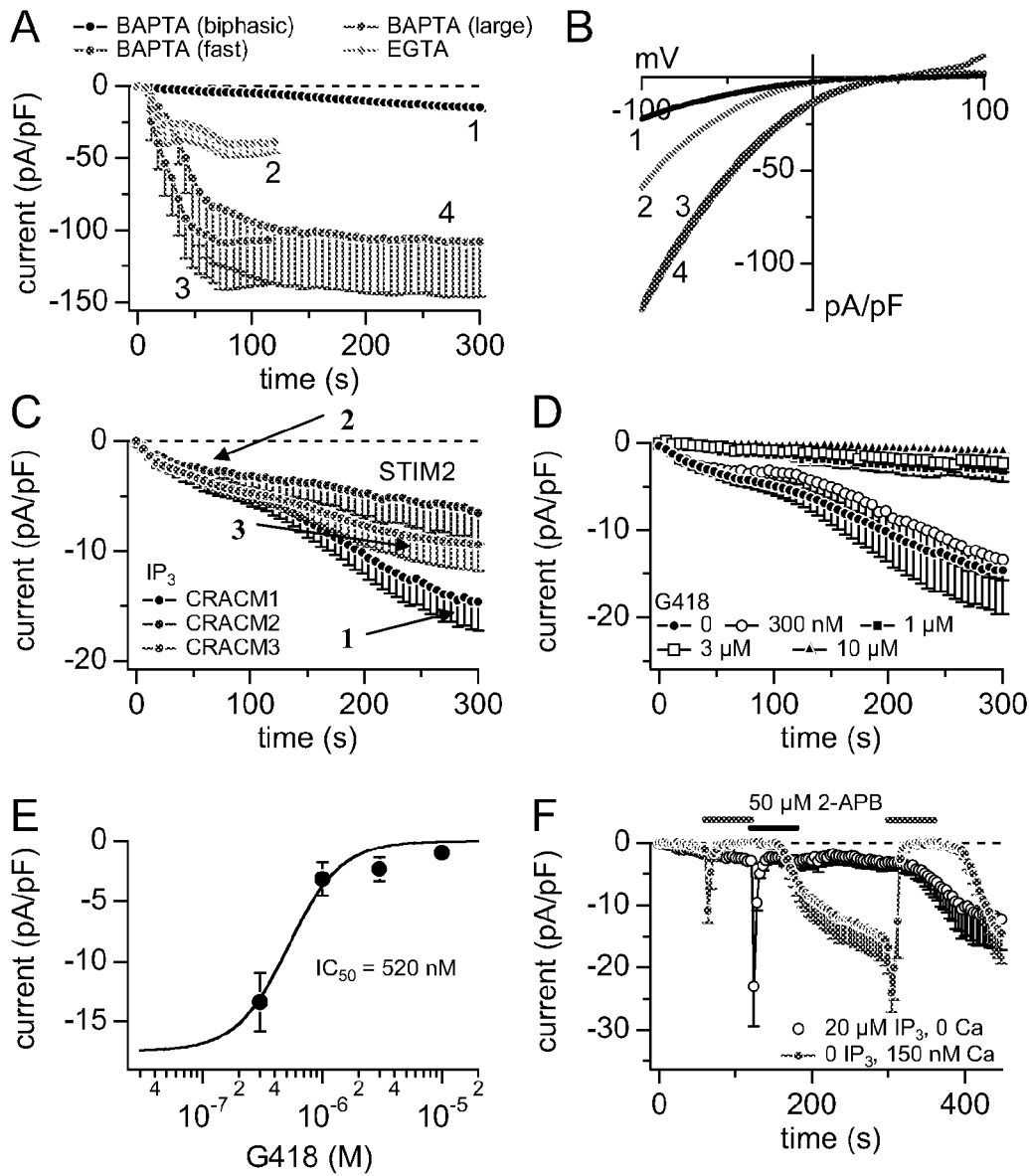
FIG. 2: Data are from HEK293 cells grown without G418. (A) Examples of average CRAC current densities in STIM2+ CRACM1 cells in response to 20 µM $IP_3$. Data are from different transfections, demonstrating the various current phenotypes observed. The predominant phenotype was small biphasic with fast primary and slow secondary phase (1). Other transfections had variable amplitudes and kinetics of the two phases. (B) Average current-voltage (I/V) relationships of CRAC currents extracted from representative STIM2+CRACM1 cells shown in panel A at 120 s or 300 s in to the experiment. Data represent leak-subtracted currents evoked by 50 ms voltage ramps from −100 to +100 mV, normalized to cell capacitance (pA/pF). (C) Average CRAC current densities induced by 20 µM $IP_3$ in STIM2-expressing HEK293 cells transfected with CRACM1 (1), CRACM2 (2) and CRACM3 (3) with $[Ca^{2+}]_i$ clamped to near zero with 20 mM BAPTA. (D) Average CRAC current densities in STIM2+CRACM1 cells in the absence of G418 (closed circles, n=34) or presence of 300 nM (open circles, n=9), 1 µM (closed squares, n=11), 3 µM (open squares, n=8), or 10 µM (closed triangles, n=8) of G418 in the pipette. (E) Dose-response relationship of average CRAC current densities as a function of G418 concentration extracted at 300 s from the recordings shown in panel D. The data were fitted with a dose-response curve, yielding an $IC_{50}$ value of 520 nM and a Hill coefficient of 1. (F) Average CRAC current densities in STIM2+CRACM1 cells stimulated by 50 µM 2-APB where store depletion was induced by 20 µM $IP_3$ and $[Ca^{2+}]_i$ buffered to near zero by 20 mM BAPTA (n=5), or prevented by omission of $IP_3$ and buffering $[Ca^{2+}]_i$ to 150 nM (n=7). Applications of 50 µM 2-APB in the two data sets are indicated by the bars.

The behavior of STIM2 was complicated by a pharmacological effect caused by the aminoglycoside antibiotic G418, which routinely was used in the growth medium to maintain selection pressure on cells stably transfected with STIM1 or STIM2. The presence of G418 did not compromise STIM1-dependent activation of CRACM1 currents, since STIM1 cells grown in G418 produce CRACM1 currents (see FIG. 1A) with similar properties as those produced by co-expression of STIM1 and CRACM1 in wt HEK293 cells that remained unexposed to G418. However, STIM2-mediated signaling was in fact compromised by G418. STIM2 overexpressing HEK293 cells grown for several days or weeks in the absence of G418 exhibited enhanced responses to 2-APB and strikingly different responses to store depletion. FIG. 1, C and D, demonstrate that these cells respond with significantly faster kinetics and with larger current amplitudes to 50 µM 2-APB. The most significant difference, however, was that these cells now responded to $IP_3$-induced store depletion by generating amplified CRAC currents of various shapes and amplitudes (FIG. 2A). The predominant CRAC current phenotype observed in most cells was characterized by a biphasic activation pattern, consisting of a small, fast activation phase that was followed by a slower phase setting in after ~100 s and rarely reached steady state even after 600 s (see also FIG. 2C and FIG. 3). For this biphasic phenotype, current amplitudes at −80 mV obtained 300 s into the experiment were about −15 pA/pF. However, in some transfections and cell populations, larger currents of up to −120 pA/pF and predominantly fast activation kinetics were observed, as if the secondary phase was relatively small or absent (see FIG. 2A for examples). In all these cases, the currents that were activated by $IP_3$ had I/V curves typical of CRAC currents (FIG. 2B).

Since the cells grown in the absence of G418 responded to $IP_3$-induced store depletion, the inhibitory effect of this antibiotic on STIM2-mediated activation of CRACM1 could be assessed by perfusing cells with defined concentrations of G418. FIG. 2D illustrates the dose-dependent inhibition of both phases of the $IP_3$-induced CRACM1 currents by increasing concentrations of G418, resulting in a half-maximal inhibitory concentration of 0.5 µM (FIG. 2E). Under identical experimental conditions, where 10 µM G418 was perfused intracellularly, it did not modify $IP_3$-induced CRAC currents in STIM1 and CRACM1 co-expressing cells (see FIG. 5). While the most potent effect of G418 appears to be mediated from the intracellular space and specifically affects STIM2-expressing cells, there was also some inhibition by the aminoglycoside when applied at 10 µM from the extracellular side. This effect, however, did not seem to be specific for STIM2, since it was similar in both STIM1- and STIM2-expressing cells (FIGS. 5 and 6), suggesting that it might be a pharmacological effect on CRACM1. The specific and potent inhibition of STIM2-mediated CRAC currents caused by intracellular G418 (and possibly other aminoglycoside antibiotics) is thus a powerful pharmacological tool to assess STIM2 function in native cell systems.

Example IV

Investigation of Cytosolic Factor with Effect CRAC Channel and STIM1 and STIM2 Activity 2-APB activates CRAC currents in STIM2- and CRACM1-expressing cells and is also capable of overcoming the G418-mediated suppression regardless of the filling state of stores. The effects of 2-APB in STIM2- and CRACM1-expressing cells that were grown in the absence of G418 were assessed using experimental protocols in which store depletion was actively induced by $IP_3$ or prevented by perfusing cells with $IP_3$-free solutions and $[Ca^{2+}]_i$ buffered to 150 nM (FIG. 2F). In both cases, 50 µM 2-APB was able to activate large, transient CRAC currents, presumably by recruitment of store-independent, pre-coupled STIM2 and CRACM1 complexes (see also FIG. 1C). Interestingly, after washout of 2-APB, the CRAC currents reactivated and remained active for the duration of the experiment, regardless of whether stores were empty or remained full. If the secondary phase of the current were due to store depletion, it should have reactivated in the case of $IP_3$-perfused cells, but not in cells with full stores.

Whether the secondary phase was in fact due to store depletion or caused by some other process was investigated. FIG. 3A illustrates that CRAC currents that developed during active store depletion by $IP_3$ (in the presence of 20 mM BAPTA to buffer $[Ca^{2+}]_i$ to near zero) had the typical biphasic activation of CRACM1 currents. When perfusing cells with pipette solutions that contained only 20 mM BAPTA to induce passive store depletion, the fast phase of CRAC current was abolished and only the secondary phase was observed, consistent with a store-dependent activation. However, perfusion of cells with an $IP_3$-free solution and $[Ca^{2+}]_i$ buffered to 150 nM to avoid store depletion still generated the slow secondary phase. These results suggest that the first phase is caused by store depletion, but the secondary phase develops regardless of the filling state of intracellular store. Hence, the secondary phase is either activated by some ingredient of our pipette filling solution or it is caused by the loss of some cytosolic factor that constitutively suppresses CRAC channels.

These possibilities were investigated by exchanging the major ingredients of the standard pipette filling solution. As shown in FIG. 3B, complete substitution of the primary intracellular salt Cs-glutamate by KCl was ineffective in suppressing the secondary current component induced by $IP_3$ and substituting the main chelator BAPTA by equimolar concentrations of EGTA failed to suppress the secondary phase in cells where store depletion was prevented by buffering $[Ca^{2+}]_i$ to 150 nM. Thus, the secondary CRAC current phase is likely to result from the washout of an as yet unidentified cellular factor.

To confirm that a cytosolic factor was activating the secondary current component, pipette tip diameters were varied and the resultant biphasic currents were analyzed. Smaller pipette tips (with higher series resistance) will reduce the rate of diffusional escape of the cytosolic inhibitor and FIG. 3C demonstrates that this indeed delayed the development of the secondary phase. The cytosolic factor does not appear to be either of the two major cytosolic nucleotides, since adding physiological concentrations of ATP (3 mM) and GTP (0.3 mM) failed to suppress the secondary phase. Likewise, the secondary phase was observed in cells perfused with 100 µM calmodulin (FIG. 3B).

Figure 3:
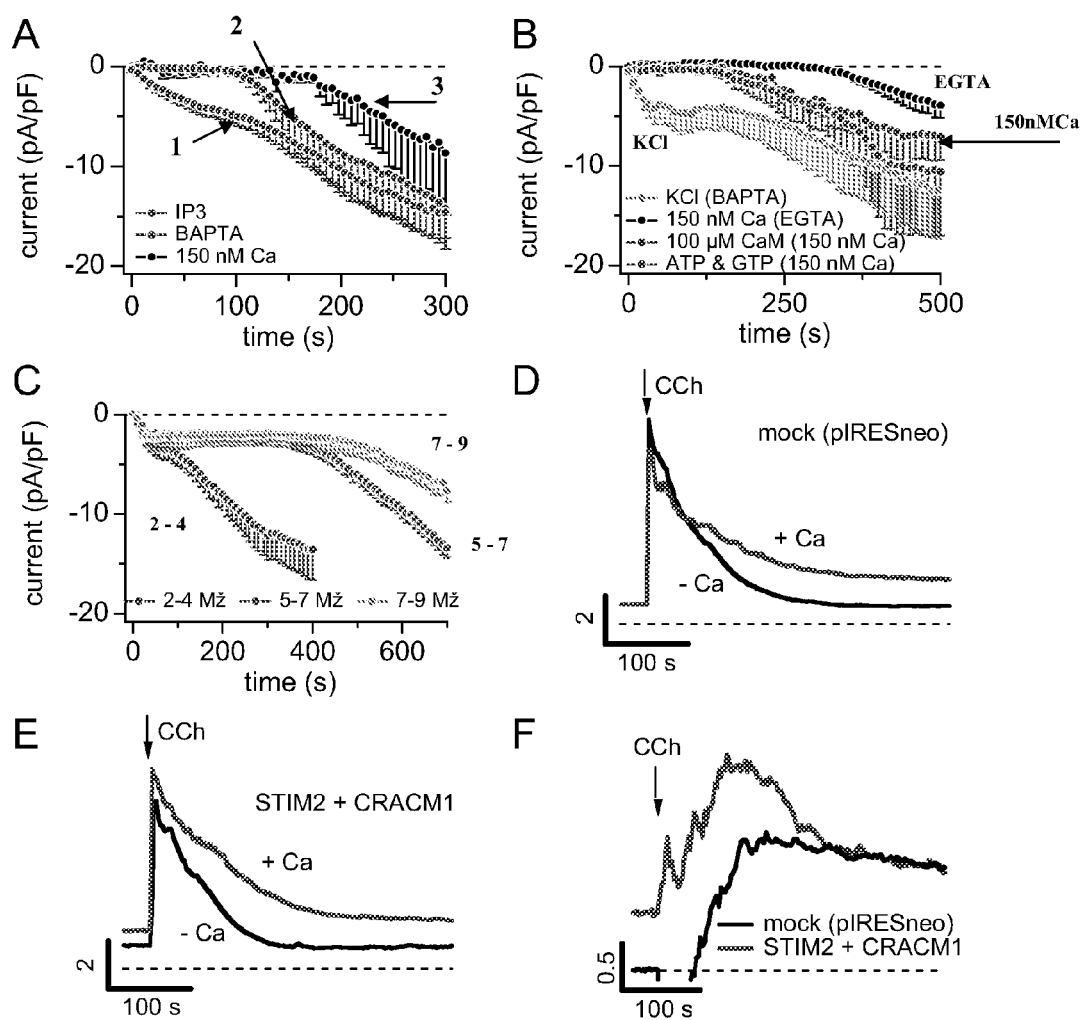
FIG. 3: Data are from HEK293 cells grown without G418. (A) Average CRAC current densities in STIM2+CRACM1 cells, where store depletion was induced by 20 µM $IP_3$+20 mM BAPTA (3) or passively by 20 mM BAPTA alone (2), or prevented by omission of $IP_3$ and buffering $[Ca^{2+}]_i$ to 150 nM (1) (B) Average CRAC currents in STIM2+CRACM1 cells induced by 20 µM $IP_3$+20 mM BAPTA in a solution where Cs-glutamate was replaced equimolarly by KCl, or store depletion was prevented by buffering $[Ca^{2+}]_i$ to 150 nM using 20 mM EGTA and 8.9 mM $CaCl_2$. Pipette solutions for the two other data sets used BAPTA and 8 mM $CaCl_2$ to buffer $[Ca^{2+}]_i$ to 150 nM and additionally contained 3 mM Mg-ATP and 300 µM Na-GTP or 100 µM calmodulin. (C) Average CRAC current densities in STIM2+CRACM1 cells, where store depletion was induced by 20 µM IP$_3$+20 mM BAPTA. Traces represent binned data of experiments in which pipette series resistances were within the following ranges: 2-4 MΩ, 5-7 MΩ, or 7-9 MΩ (D) Changes in [Ca$^{2+}$]$_i$ measured as ratios of fura-2 fluorescence excited at 340 and 380 nm in STIM2 cells transfected with empty vector in the absence or presence of 1 mM extracellular Ca$^{2+}$. Carbachol (100 µM) was applied as indicated by the arrow. (E) Identical experimental conditions as in panel D, but for STIM2+CRACM1 cells. (F) These traces represent subtracted traces from panels D and E, where the [Ca$^{2+}$]$_i$ signal in Ca$^{2+}$-free solution was subtracted from that obtained with Ca$^{2+}$ to yield the net Ca$^{2+}$ entry.

In intact cells, the endogenous inhibitor cannot escape and therefore, one would expect the initial store-operated activation of CRAC channels by STIM2 to be followed by inhibition, resulting in a transient store-operated $Ca^{2+}$ entry phase. This was tested in intact cells loaded with the $Ca^{2+}$ indicator fura-2 and stimulated store-operated $Ca^{2+}$ influx through muscarinic receptors using carbachol. This experiment was performed both in the presence and absence of extracellular $Ca^{2+}$ and in stable STIM2-expressing HEK293 cells that were transiently transfected with an empty vector or with CRACM1. As illustrated in FIG. 3, D and E, the empty vector-transfected and CRACM1-overexpressing cells produced a transient increase in $[Ca^{2+}]_i$ that was independent of extracellular $Ca^{2+}$ due to $IP_3$-mediated release of $Ca^{2+}$ from intracellular stores. As expected, the presence of extracellular $Ca^{2+}$ produced a plateau phase of elevated $[Ca^{2+}]_i$ that is due to store-operated $Ca^{2+}$ entry in both cell populations. However, the CRACM1-expressing cells exhibited a more pronounced shoulder following the release transient due to store-operated activation by STIM2.

To further elucidate the differences in $Ca^{2+}$ entry between the two populations, signals obtained in the absence of $Ca^{2+}$ were subtracted from those in the presence of $Ca^{2+}$ to arrive at the net influx components in the two cell populations. As can be seen in FIG. 3F, the CRACM1-expressing cells produced a transient increase in store operated calcium entry that decayed to similar levels as those in empty vector-transfected cells. This transient increase in store operated calcium entry reflects the store-operated $Ca^{2+}$ entry induced by STIM2 coupling to CRACM1 channels following store depletion.

What is claimed is:

1. An assay for Stromal Interaction Molecule 2 (STIM2) activity in a cell comprising applying 2-aminoethoxy diphenyl borate (2-APB) in the absence of calcium store depletion to a cell, measuring the Calcium Release Activated Calcium Current ($I_{crac}$)[crac] activity of the cell, wherein an increase in $I_{crac}$[crac] activity in response to application of 2-APB indicates a level of STIM2 activity in the cell.

2. The assay of claim 1, wherein said cell is derived from a mammalian subject.

3. The assay of claim 2, wherein said cell is derived from the brain of said mammalian subject.

4. An assay for agents that modulate Stromal Interaction Molecule 2 (STIM2) activity, the assay comprising applying 2-aminoethoxy diphenyl borate (2-APB) in the absence of calcium store depletion to a cell, measuring $I_{crac}$ activity in response to application of 2-APB in the absence of calcium store depletion, wherein an agent that modulates the $I_{crac}$ activity is identified as an agent that modulates STIM2 activity.

5. An assay for measuring relative Stromal Interaction Molecule 2 (STIM2) activity, the assay comprising measuring Calcium Release Activated Calcium Current ($I_{crac}$) activity in a first cell type, wherein an increase in $I_{crac}$ activity in response to application of 2-aminoethoxy diphenyl borate (2-APB) in the absence of calcium store depletion indicates a level of STIM2 activity in the first cell type, measuring $I_{crac}$ activity in a second cell type, wherein an increase in $I_{crac}$ activity in response to application of 2-aminoethoxy diphenyl borate (2-APB) in the absence of calcium store depletion indicates a level of STIM2 activity in the second cell type, and comparing the level of STIM2 activity in the first cell type to the level of STIM2 activity in the second cell type.

6. The assay of claim 5, wherein the second cell type is derived from the brain of a mammalian subject.

* * * * *